US010835505B2

(12) United States Patent
Lee

(10) Patent No.: US 10,835,505 B2
(45) Date of Patent: Nov. 17, 2020

(54) ORAL PHARMACEUTICAL FORMULATION FOR WEIGHT LOSS, DIABETES AND RELATED DISORDERS

(71) Applicant: Tien-Li Lee, San Diego, CA (US)

(72) Inventor: Tien-Li Lee, San Diego, CA (US)

(73) Assignee: Aardvark Therapeutics, Inc., San Diego, CA (US)

(*) Notice: Subject to any disclaimer, the term of this patent is extended or adjusted under 35 U.S.C. 154(b) by 136 days.

(21) Appl. No.: 16/004,700

(22) Filed: Jun. 11, 2018

(65) Prior Publication Data
US 2019/0374489 A1  Dec. 12, 2019

(51) Int. Cl.
| | | |
|---|---|---|
| A61K 31/192 | (2006.01) | |
| A61P 3/04 | (2006.01) | |
| A61K 31/365 | (2006.01) | |
| A61K 31/165 | (2006.01) | |

(52) U.S. Cl.
CPC .......... *A61K 31/192* (2013.01); *A61K 31/165* (2013.01); *A61K 31/365* (2013.01); *A61P 3/04* (2018.01)

(58) Field of Classification Search
CPC .. A61K 31/192; A61K 31/165; A61K 31/365; A61P 3/04
See application file for complete search history.

(56) References Cited

U.S. PATENT DOCUMENTS

| | | | |
|---|---|---|---|
| 7,655,256 B2 * | 2/2010 | Hughes ................ | A61K 9/2013 424/454 |
| 7,939,671 B2 | 5/2011 | Li | |
| 8,445,692 B2 | 5/2013 | Karanewsky | |
| 8,796,233 B2 | 8/2014 | Goddard | |
| 9,272,051 B2 | 3/2016 | Goddard | |
| 10,330,678 B2 | 6/2019 | Goddard | |
| 2003/0198666 A1 * | 10/2003 | Abbas .................. | A61K 9/2013 424/452 |
| 2011/0091509 A1 * | 4/2011 | Howard ............... | A61K 9/2027 424/400 |
| 2014/0030332 A1 | 1/2014 | Baron | |
| 2014/0302528 A1 | 10/2014 | Li | |
| 2017/0067000 A1 * | 3/2017 | Brandt-Sanz ....... | C11D 11/0017 |
| 2018/0161298 A1 | 6/2018 | Deretic | |

FOREIGN PATENT DOCUMENTS

WO    WO-2016172479 A1 * 10/2016    ............. A61K 38/08

OTHER PUBLICATIONS

Zhai et al. "Activation of bitter taste receptors (tas2rs) relaxes detrusor smooth muscle and suppresses overactive bladder symptoms" Oncotarget :21156-21167, 2016.
Deckmann et al., "Bitter triggers acetylcholine release from polymodal urethral chemosensory cells and bladder reflexes" Proc. Natl. Acad. Sci. 111:8287-8292, 2014.
Manson et al., "Bitter taste receptor agonists mediate relaxation of human and rodent vascular smooth muscle" Eur. J. Phamacology 740:302-311, 2014.
Pulkkinen et al., "The bitter taste receptor (TAS2R) agonists denatonium and chloroquine display distinct patterns of relaxation of the guinea pig trachea" Am. J. Physiol. Lung Cell Mol. Physiol. 303:956-966, 2012.
Sai et al. "Bitter tastants induce relaxation of rat thoracic aorta precontracted with high K+" Clin. Exper. Pharmacology and Phys. 41:301-301, 2014.
Gassin-Delyle et al., "The expression and relaxant effect of bitter taste receptors on human bronchi" Respiratory Research 14:134, 2013.
Deloose et al. "Intragastric infusion of denatonium benzoate attenuates interdigestive gastric motility and hunger scores in healthy female volunteers1" Am. J. Clin. Nutr. 105:583-588, 2017.
Avau et al. "Targeting extra-oral bitter taste receptors modulates gastrointestinal motility with effects on satiation" Scientific Reports 5:15985 2015.
Avau et al.2 "The Gustatory Signaling Pathway and Bitter Taste Receptors Affect the Development of Obesity and Adipocyte Metabolismi n Mice" PLOS One 10.1371 2015.
Glendinning et al., "Intragastric infusion of denatonium conditions flavor aversions and delays gastric emptying in rodents" Physiol. Behav. 93:757-765, 2008.
Hao et al., "Role of CCK1 and Y2 receptors in activation of hindbrain neurons induced by intragastric administration of bitter taste receptor ligands" Am. J. Physiol. Regul. Integr. Comp. Physiol. 294:R33-R38, 2008.
Janssen et al., "Bitter taste receptors and α-gustducin regulate the secretion of ghrelin with functional effects on food intake and gastric emptying" PNAS 108:2094-2099, 2011.
Kim et al., "Denatonium induces secretion of glucagon-like peptide-1 through activation of bitter taste receptor pathways" Diabetologia 57:2117-2125, 2014.
Miyata et al. "Effect of five taste ligands on the release of CCK from an enteroendocrine cell line, STC-1" Biomedical Research 35:171-176, 2014.
Schier et al. "Ongoing ingestive behavior is rapidly suppressed by a preabsorptive, intestinal "bitter taste" cue" Am. J. Physiol. Regul. Integr. Comp. Physiol. 301:R1557-R1568, 2011.

(Continued)

*Primary Examiner* — Ali Soroush
(74) *Attorney, Agent, or Firm* — Jeffrey B. Ostor

(57) ABSTRACT

There is disclosed an oral pharmaceutical formulation of bitter compounds that are agonists of taste receptor type 2 (TAS2R) receptors for the function of appetite suppression for the treatment of obesity. More specifically, the present disclosure provides an anti-obesity oral formulation comprising a bitter agent selected from the group consisting of denatonium salts including benzoate (DB), chloride (DC), acetate (DA), citrate (DCl), saccharide (DS), tartarate (DT), maleate (DM), 3-caffeoylquinic-1,5-lactone (3-CQL), chlorogenic acids (CGA), combinations thereof, and pharmaceutical excipients to facilitate a sustained release during transit through the gastrointestinal (GI) tract. Preferably, the oral pharmaceutical formulation further comprises either or both a sweet antagonist selected from the group consisting of lactisole, gymnemic acid, ziziphin, hodulcine, and combinations thereof, and a sour organic acid.

19 Claims, 5 Drawing Sheets

(56) References Cited

OTHER PUBLICATIONS

Straub et al., "Stimulation of Insulin Secretion by Denatonium, One of the Most Bitter-Tasting Substances Known" Diabetes 52:356-364, 2003.

Upadhyaya et al., PLOS One 9:e110373, Dextromethorphan Mediated Bitter Taste Receptor Activation in the Pulmonary Circuit Causes Vasoconstriction.

* cited by examiner

ORAL PHARMACEUTICAL FORMULATION FOR WEIGHT LOSS, DIABETES AND RELATED DISORDERS

CROSS REFERENCE TO RELATED APPLICATIONS

This patent application claims priority to U.S. provisional patent application 62/517,831 filed 9 Jul. 2017, and U.S. provisional patent application 62/631,80 filed 18 Feb. 2018.

TECHNICAL FIELD

The present disclosure provides an oral pharmaceutical formulation of bitter compounds that are agonists of taste receptor type 2 (TAS2R) receptors for the function of appetite suppression for the treatment of obesity. More specifically, the present disclosure provides an anti-obesity oral formulation comprising a bitter agent selected from the group consisting of denatonium salts including benzoate (DB), chloride (DC), acetate (DA), citrate (DCl), saccharide (DS), tartarate (DT), maleate (DM), 3-caffeoylquinic-1,5-lactone (3-CQL), chlorogenic acids (CGA), combinations thereof, and pharmaceutical excipients to facilitate a sustained release during transit through the gastrointestinal (GI) tract. Preferably, the oral pharmaceutical formulation further comprises either or both a sweet antagonist selected from the group consisting of lactisole, gymnemic acid, ziziphin, hodulcine, and combinations thereof, and a sour organic acid.

BACKGROUND

Chemosensory signaling of nutrients plays a vital role in regulating appetite, digestion, and metabolism. In particular, a variety of bitter taste receptors (TAS2R family of G-protein-coupled receptors (GPCRs)) exist not only in the oral cavity, but on gut endocrine cells, human gastric smooth muscle cells, adipocytes, as well as sites in the chemoreceptor trigger zone in the medulla of the brain.

There are approximately 25 known TAS2R subtypes, which are GPCRs. It is believed that these bitter taste receptors exist to serve as toxicity detectors, as they broadly detect alkaloid compounds, which are often poisonous. In the oral cavity, bitter taste perception is an aversive stimulus and discourages ingestion of food if bitterness is detected at a sufficiently high level. However, in the gut and brain, detection of alkaloid compounds by TAS2R receptors induce impaired fundic relaxation of the stomach, a slow-down of gastric emptying, and increase satiation, ostensibly to limit ingestion and prolong the absorption and processing of food perceived as toxic. TAS2Rs are also expressed in white adipose tissue, stimulation of which has been experimentally observed to decrease differentiation of pre-adipocytes into mature adipocytes, decrease lipid accumulation, among other observed metabolic effects.

Obesity is ideally treated with dieting and physical exercise, but success rates for such programs have been observed to be low, at approximately 20%. Often, this is largely due to a strong appetite drive which has redundant stimulatory pathways and is difficult to overcome, as suppression of one pathway for appetite generation frequently results in upregulation of compensatory alternate pathways to invoke hunger over time. Various medications that have been commercially available confer generally modest results or have accompanying risk and side effects that are deemed intolerable by many, or both.

Anorexigenic stimulant compounds such as ephedrine, fenfluramine, and dexfenfluramine were withdrawn from the market due to associated cardiovascular safety risks. Drugs that interfere with nutrient absorption such as Orlistat, a lipase inhibitor, which blocks fat processing in the gut, results in oily stool and diarrhea. Central nervous system targeted drugs such as Sibutramine (a monoamine oxidase inhibitor), Rimonabant (a cannabinoid receptor antagonist), and others, have significant central nervous system (CNS) "off-target" effects often leading to unintended psychiatric or neurological manifestations.

Therefore, there is a need in the art to utilize such taste receptor agonists in order to provide safer and effective weight loss therapeutics. The present disclosure was made to utilize such TAS2R agonists to suppress appetite and cause resulting weight loss.

SUMMARY

The present disclosure provides formulations of bitter compounds that are agonists for TAS2R receptors for the function of appetite suppression for the treatment of obesity. More specifically, the present disclosure provides an anti-obesity oral formulation comprising a bitter agent selected from the group consisting of denatonium salts including benzoate (DB), chloride (DC), acetate (DA), citrate (DCl), saccharide (DS), tartarate (DT), maleate (DM), 3-caffeoylquinic-1,5-lactone (3-CQL), chlorogenic acids (CGA), combinations thereof. Preferably, the oral pharmaceutical formulation further comprises either or both a sweet antagonist selected from the group consisting of lactisole, gymnemic acid, ziziphin, hodulcine, and combinations thereof, and a sour organic acid. Preferably the oral formulation further comprises pharmaceutical excipients to facilitate a sustained release during transit through the GI tract. Preferably the dosage per day for an adult of the sweet antagonist is from about 50 mg to about 1.50 g. More preferably, the dosage per day of the sweet antagonist for an adult is from about 60 mg to about 1.0 g. Still more preferably, the dosage per day of the sweet antagonist for an adult is from about 75 mg to about 0.50 g. Most preferably, the sweet antagonist is lactisole.

The present disclosure further provides an anti-obesity oral formulation comprising a bitter agent selected from the group consisting of denatonium salts including benzoate (DB), chloride (DC), acetate (DA), citrate (DCl), saccharide (DS), tartarate (DT), maleate (DM), 3-caffeoylquinic-1,5-lactone (3-CQL), chlorogenic acids (CGA), combinations thereof. Preferably, the oral formulation further comprises a sweet antagonist selected from the group consisting of lactisole, gymnemic acid, ziziphin, hodulcine, and combinations thereof and pharmaceutical excipients to facilitate a sustained release during transit through the GI tract. Preferably, the oral formulation further comprises an organic acid selected from the group consisting of acetic acid, malic acid, maleic acid, citric acid and combinations thereof. Preferably the dosage per day for an adult of the sweet antagonist is from about 50 mg to about 1.50 g. More preferably, the dosage per day of the sweet antagonist for an adult is from about 60 mg to about 1.0 g. Still more preferably, the dosage per day of the sweet antagonist for an adult is from about 75 mg to about 0.50 g. Most preferably, the sweet antagonist is lactisole.

Preferably the dosage per day for an adult of the organic acid is from about 0.5 g to about 5 g. More preferably, the dosage per day of the organic acid for an adult is from about 1.5 g to about 3 g. Most preferably, the organic acid is acetic acid.

Preferably the bitter agent is a denatonium salt or 3-CQL. Preferably the daily dosage of the denatonium salt for an adult is from about 10 mg to about 400 mg. More preferably, the daily dosage of the denatonium salt for an adult is from about 10 mg to about 200 mg. Most preferably, the daily dosage of the denatonium salt for an adult is from about 10 mg to about 100 mg, or to achieve a concentration in the GI tract of from about 10 parts per billion to about 10 ppm.

Further, the present disclosure provides a sustained release oral formulation comprising a denatonium salt, lactisole, and acetic acid powder in a sustained release cellulosic and mannitol excipient formulation. Preferably, the dosage per day for an adult of the sweet antagonist component of the oral formulation is from about 50 mg to about 1.50 g. More preferably, the dosage per day of the sweet antagonist component of the oral formulation for an adult is from about 60 mg to about 1.0 g. Still more preferably, the dosage per day of the sweet antagonist component of the oral formulation for an adult is from about 75 mg to about 0.50 g. Most preferably, the sweet antagonist is lactisole. Most preferably the bitter agent is selected from the group consisting of DA, DC, and 3-CQL. Preferably, the dosage per day for an adult of the organic acid is from about 0.5 g to about 5 g. More preferably, the dosage per day of the organic acid for an adult is from about 1.5 g to about 3 g. Preferably the daily dosage of DB for an adult is from about 10 mg to about 400 mg. More preferably, the daily dosage of DB for an adult is from about 10 mg to about 200 mg. Most preferably, the daily dosage of DB for an adult is from about 10 mg to about 100 mg, or to achieve a concentration in the GI tract of from about 10 parts per billion to about 10 ppm. Preferably, the oral formulation comprises from about 0.01% to about 10 wt % DA or DC, from about 0.01 to about 10 wt % lactisole, and from about 10% to about 90 wt % dry acetic acid powder. Preferably, the dose administered of DA or DC is from about 500 nmol/kg to about 10 μmol/kg. Preferably, the dose administered of DA or DC is from about 10 mg to about 200 mg for an adult.

The present disclosure further provides a method for effecting weight loss, comprising administering an anti-obesity oral formulation comprising a bitter agent selected from the group consisting of denatonium salts including benzoate (DB), chloride (DC), acetate (DA), citrate (DCl), saccharide (DS), tartarate (DT), maleate (DM), 3-caffeoylquinic-1,5-lactone (3-CQL), chlorogenic acids (CGA), combinations thereof. Preferably, the method further comprises administering either a sweet antagonist selected from the group consisting of lactisole, gymnemic acid, ziziphin, hodulcine, and combinations thereof; or an organic acid selected from the group consisting of acetic acid, malic acid, maleic acid, citric acid and combinations thereof; and pharmaceutical excipients to facilitate a sustained release during transit through the GI tract. Preferably, the dosage per day for an adult of the sweet antagonist is from about 50 mg to about 1.50 g. More preferably, the dosage per day of the sweet antagonist for an adult is from about 60 mg to about 1.0 g. Still more preferably, the dosage per day of the sweet antagonist for an adult is from about 75 mg to about 0.50 g. Most preferably, the sweet antagonist is lactisole. Preferably the dosage per day for an adult of the organic acid is from about 0.5 g to about 5 g. More preferably, the dosage per day of the organic acid for an adult is from about 1.5 g to about 3 g. Most preferable, the organic acid is acetic acid. Preferably the bitter agent is DA or DC. Preferably the daily dosage of DA or DC for an adult is from about 10 mg to about 400 mg. More preferably, the daily dosage of DA or DC for an adult is from about 10 mg to about 200 mg. Most preferably, the daily dosage of DA or DC for an adult is from about 10 mg to about 100 mg, or to achieve a concentration in the GI tract of from about 10 parts per billion to about 10 ppm.

The present disclosure further provides a method for treating or preventing adult onset diabetes as measured by HbA1c and or insulin and or low density lipoprotein (LDL) cholesterol levels, comprising administering a bitter agent selected from the group consisting of denatonium salts including benzoate (DB), chloride (DC), acetate (DA), citrate (DCl), saccharide (DS), tartarate (DT), maleate (DM), 3-caffeoylquinic-1,5-lactone (3-CQL), chlorogenic acids (CGA), combinations thereof. Preferably, the method further comprises administering either a sweet antagonist selected from the group consisting of lactisole, gymnemic acid, ziziphin, hodulcine, and combinations thereof; or an organic acid selected from the group consisting of acetic acid, malic acid, maleic acid, citric acid and combinations thereof; and pharmaceutical excipients to facilitate a sustained release during transit through the GI tract. Preferably, the dosage per day for an adult of the sweet antagonist is from about 50 mg to about 1.50 g. More preferably, the dosage per day of the sweet antagonist for an adult is from about 60 mg to about 1.0 g. Still more preferably, the dosage per day of the sweet antagonist for an adult is from about 75 mg to about 0.50 g. Most preferably, the sweet antagonist is lactisole. Preferably the dosage per day for an adult of the organic acid is from about 0.5 g to about 5 g. More preferably, the dosage per day of the organic acid for an adult is from about 1.5 g to about 3 g. Most preferably, the organic acid is acetic acid. Preferably the bitter agent is DA or DC. Preferably the daily dosage of DA or DC for an adult is from about 10 mg to about 400 mg. More preferably, the daily dosage of DA or DC for an adult is from about 10 mg to about 200 mg. Most preferably, the daily dosage of DA or DC for an adult is from about 10 mg to about 100 mg, or to achieve a concentration in the GI tract of from about 10 parts per billion to about 10 ppm.

DETAILED DESCRIPTION

Figure 1:
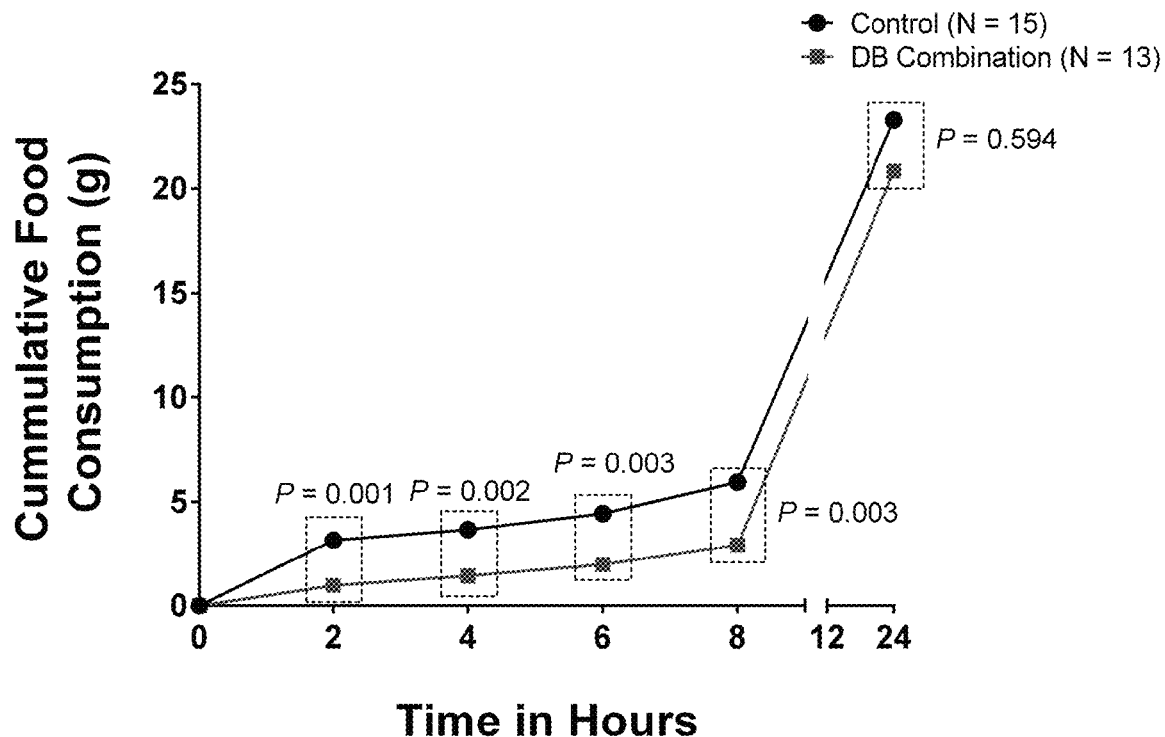
FIG. 1 shows average cumulative food consumption over 24 hours measured for an acute food intake inhibition study at time 0, 2, 4, 6, 8 and 24 hours after a single administration of the disclosed formulation in Sprague Dawley (SD) rats. The figure shows that at all time points in the first 8 hours the animals given water control consumed significantly more food than those receiving disclosed formulation.

The present disclosure provides formulations of bitter compounds that are agonists for TAS2R receptors for the function of appetite suppression for the treatment of obesity. More specifically, the present disclosure provides an anti-obesity oral formulation comprising (a) a a bitter agent selected from the group consisting of denatonium benzoate (DB), denatonium chloride, denatonium saccharide, quinine, chloroquine, cromolyn, diphenidol, amarogentin, apomorphine, parthenolide, camphor, arborescin, artemorin, divinyl sulfoxide, picrotoxinin, aristolochic acid, falcarindiol, 3-caffeoylquinic-1,5-lactone (3-CQL), chlorogenic acids (CGA), hydroxycinnamic acids, caffeic acid, ferulic acid, p-coumaric acid. and combinations thereof; (b) a sweet antagonist selected from the group consisting of lactisole, gymnemic acid, ziziphin, hodulcine, and combinations thereof; and (c) pharmaceutical excipients to facilitate a sustained release during transit through the GI tract. Preferably, the oral formulation further comprises an organic acid selected from the group consisting of acetic acid, malic acid, maleic acid, citric acid and combinations thereof. Preferably, the dosage per day for an adult of the sweet antagonist is from about 50 mg to about 1.50 g. More preferably, the dosage per day of the sweet antagonist for an adult is from about 60 mg to about 1.0 g. Still more preferably, the dosage per day of the sweet antagonist for an adult is from about 75 mg to about 0.50 g. Most preferably, the sweet antagonist is lactisole. Preferably the dosage per day for an adult of the organic acid is from about 0.5 g to about 5 g. More preferably, the dosage per day of the organic acid for an adult is from about 1.5 g to about 3 g. Most preferably, the organic acid is acetic acid. Preferably the bitter agent is DB. Preferably the daily dosage of DB for an adult is from about 10 mg to about 400 mg. More preferably, the daily dosage of DB for an adult is from about 10 mg to about 200 mg. Most preferably, the daily dosage of DB for an adult is from about 10 mg to about 100 mg, or to achieve a concentration in the GI tract of from about 10 parts per billion to about 10 ppm.

Further, the present disclosure provides a sustained release oral formulation comprising DB, lactisole, and acetic acid powder in a sustained release cellulosic and mannitol excipient formulation. Preferably, the dosage per day for an adult of the sweet antagonist is from about 50 mg to about 1.50 g. More preferably, the dosage per day of the sweet antagonist for an adult is from about 60 mg to about 1.0 g. Still more preferably, the dosage per day of the sweet antagonist for an adult is from about 75 mg to about 0.50 g. Most preferably, the sweet antagonist is lactisole. Most preferably the bitter agent is DB. Preferably the daily dosage of DB for an adult is from about 10 mg to about 400 mg. More preferably, the daily dosage of DB for an adult is from about 10 mg to about 200 mg. Most preferably, the daily dosage of DB for an adult is from about 10 mg to about 100 mg, or to achieve a concentration in the GI tract of from about 10 parts per billion to about 10 ppm. Preferably, the oral formulation comprises from about 0.01% to about 10 wt % DB, from about 0.01 to about 10 wt % lactisole, and from about 10% to about 90 wt % dry acetic acid powder. Preferably, the dose administered of DB is from about 500 nmol/kg to about 4 µmol/kg. Preferably, the dose administered of DB is from about 10 mg to about 50 mg for an adult.

The present disclosure further provides a method for effecting weight loss, comprising administering an anti-obesity oral formulation comprising (a) a bitter agent selected from the group consisting of denatonium benzoate (DB), denatonium chloride, denatonium saccharide, quinine, chloroquine, cromolyn, amarogentin, parthenolide, diphenidol, apomorphine, camphor, arborescin, artemorin, divinyl sulfoxide, picrotoxinin, aristolochic acid, falcarindiol, 3-caffeoylquinic-1,5-lactone (3-CQL), chlorogenic acid (CGA), and combinations thereof; (b) a sweet antagonist selected from the group consisting of lactisole, gymnemic acid, ziziphin, hodulcine, and combinations thereof; and (c) pharmaceutical excipients to facilitate a sustained release during transit through the GI tract. Preferably, the oral formulation further comprises an organic acid selected from the group consisting of acetic acid, malic acid, maleic acid, citric acid and combinations thereof. Preferably, the dosage per day for an adult of the sweet antagonist is from about 50 mg to about 1.50 g. More preferably, the dosage per day of the sweet antagonist for an adult is from about 60 mg to about 1.0 g. Still more preferably, the dosage per day of the sweet antagonist for an adult is from about 75 mg to about 0.50 g. Most preferably, the sweet antagonist is lactisole. Preferably the dosage per day for an adult of the organic acid is from about 0.5 g to about 5 g. More preferably, the dosage per day of the organic acid for an adult is from about 1.5 g to about 3 g. Most preferably, the organic acid is acetic acid. Preferably the bitter agent is DB or 3-CQL. Preferably the daily dosage of DB for an adult is from about 10 mg to about 400 mg. More preferably, the daily dosage of DB for an adult is from about 10 mg to about 200 mg. Most preferably, the daily dosage of DB for an adult is from about 10 mg to about 100 mg, or to achieve a concentration in the GI tract of from about 10 parts per billion to about 10 ppm.

In a short-term food intake inhibition study, in Sprague Dawley rats the doses of DB administered were 7.5, 15, 30, and 60 µmol/kg. The corresponding human equivalent doses (HED) are be 1.2, 2.4, 4.9, 9.7 µmol/kg, respectively. In a longer-term food intake inhibition study in C57BL/6NTac mice the dose of DB used was was 60 µmol/kg. The corresponding HED was 4.9 µmol/kg. As a background, according to Avau et al. (*Sci. Rep.* (2015) 5:15985), oral administration of only denatonium benzoate (DB) at 60 µmol/kg (26.8 mg/kg) significantly inhibited gastric emptying rate in normal C57BL/6 mice. In another study, treatment with 60 µmol/kg DB (26.8 mg/kg) once daily induced a decrease in body weight of C57BL/6 DIO mice during a 28-day period, as compared to vehicle. According to Avau et al., healthy volunteers receiving 1 µmol/kg DB showed decreased nutrient volume tolerance and increased satiation. Therefore, the disclosed formulation provides a dose of DB from about 500 nmol/kg to about 10 mol/kg, which corresponds to from about 10 mg to about 200 mg for a human adult.

TABLE 1

Bitter agents

| Active name | Chemical structure |
|---|---|
| Denatonium benzoate (DB) | (structure shown) |
| Denatonium chloride | (structure shown) |
| Denatonium saccharide | (structure shown) |
| Quinine | (structure shown) |
| Chloroquine | (structure shown) |
| Cromolyn | (structure shown) |

TABLE 1-continued

Bitter agents

| Active name | Chemical structure |
|---|---|
| Amarogentin | 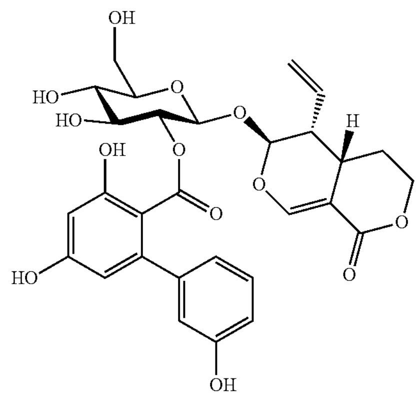 |
| Parthenolide | 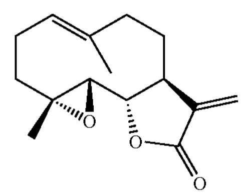 [SMILES: C=C1C(=O)O[C@H]2[C@H]1CC/C(C)=C/CC[C@@]1(C)O[C@@H]21] |
| Diphenidol | 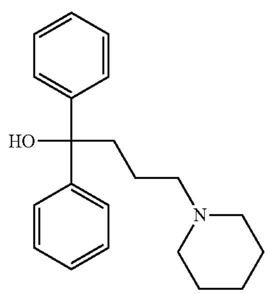 [SMILES: OC(CCCN1CCCCC1)(c1ccccc1)c1ccccc1] |
| Apomorphine | 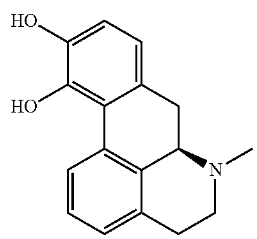 [SMILES: CN1CCc2cccc3c2[C@H]1Cc1ccc(O)c(O)c1-3] |
| D-Camphor | 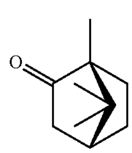 |
| Arborescin | 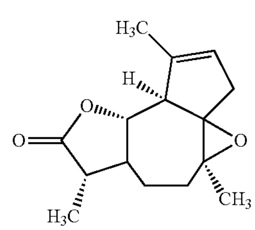 |

TABLE 1-continued

| Bitter agents | |
|---|---|
| Active name | Chemical structure |
| Artemorin | |
| Divinyl sulfoxide | |
| Picrotoxinin | |
| Aristolochic acid | |
| Falcarindiol | |
| 3-caffeoylquinic-1,5-lactone (3-CQL) | |

TABLE 1-continued

Bitter agents

| Active name | Chemical structure |
|---|---|
| Chlorogenic acid (CGA) | (structure shown) |

Denatonium Benzoate (DB)
IUPAC Name: benzyl-[2-(2,6-dimethylanilino)-2-oxoethyl]-diethylazanium benzoate
Molecular Formula: $C_{28}H_{34}N_2O_3$
Molecular Mass: 446.581 g/mol
CAS Number: 3734-33-6
ChemSpider ID:
Denatonium, usually available as denatonium benzoate (under trade names such as BITTERANT-b, BITTER+PLUS, Bitrex or Aversion) and as denatonium saccharide (BITTERANT-s), is believed to be the most bitter chemical compound known, with bitterness thresholds of 0.05 ppm for the benzoate and 0.01 ppm for the saccharide. It is used as an aversive agent (bitterants) to prevent inappropriate ingestion. Denatonium is used in denatured alcohol, antifreeze, nail biting preventions, respirator mask fit-testing, animal repellents, liquid soaps, and shampoos. It is not known to pose any long-term health risks.
Denatonium Chloride
IUPAC Name: benzyl-[2-(2,6-dimethylanilino)-2-oxoethyl]-diethylazanium chloride
Molecular Formula: $C_{21}H_{29}ClN_2O$
Molecular Mass: 360.926 g/mol
CAS Number: 1674-99-3
ChemSpider ID: 14734
Like denatonium benzoate, denatonium chloride is also one of the most bitter stimuli known in humans, with the bitterness threshold of $1\text{-}2\times10^{-8}$ mol/L.
Denatonium Saccharide
IUPAC name: benzyl-[2-(2,6-dimethylanilino)-2-oxoethyl]-diethylazanium; 1,1-dioxo-1,2-benzothiazol-3-olate
Molecular Formula: $C_{28}H_{33}N_3O_4S$
Molecular Mass: 507.649 g/mol
CAS Number: 90823-38-4
ChemSpider ID:
Denatonium saccharide is judged to be 5 times more bitter than denatonium benzoate. This compound will make a product so bitter that children and pets will not be able to swallow it. Denatonium saccharide is bitter at 1 to 10 ppm, at 30 to 100 ppm virtually any product becomes impossible to masticate.
Quinine
IUPAC Name: (R)-[(2S,4S,5R)-5-ethenyl-1-azabicyclo[2.2.2]octan-2-yl]-(6-methoxyquinolin-4-yl)methanol
Molecular Formula: $C_{20}H_{24}N_2O_2$
Molecular Mass: 324.42 g/mol
CAS Number: 130-95-0
ChemSpider ID: 84989
Quinine is a medication used to treat malaria, babesiosis, and restless leg syndrome, taken orally or intravenously, although it is often also administered intramuscularly and rectally. It is also added to tonic water to confer bitter taste.
Chloroquine
IUPAC Name: 4-N-(7-chloroquinolin-4-yl)-1-N,1-N-diethylpentane-1,4-diamine
Molecular Formula: $C_{18}H_{26}ClN_3$
Molecular Mass: 319.877 g/mol
CAS Number: 54-05-7
ChemSpider ID: 2618
Cromolyn
IUPAC Name: 5-[3-(2-carboxy-4-oxochromen-5-yl)oxy-2-hydroxypropoxy]-4-oxochromene-2-carboxylic acid
Chemical Formula: $C_{23}H_{16}O_{11}$
Molecular Mass: 468.37 g/mol
ChemSpider ID: 2779
Cromolyn (also referred to as cromolyn (United States Adopted Name, USAN), cromoglycate (former British Approved Name, BAN), or cromoglicate) is a mast cell stabilizer and can be given via several routes: topical, oral, nasal spray, inhaled, and eye drops.
Amarogentin
IUPAC name: [(2S,3R,4S,5S,6R)-2-[[(3S,4R,4aS)-4-Ethenyl-8-oxo-4,4a,5,6-tetrahydro-3H-pyrano[3,4-c]pyran-3-yl]oxy]-4,5-dihydroxy-6-(hydroxymethyl)oxan-3-yl]2,4-dihydroxy-6-(3-hydroxyphenyl)benzoate
Chemical Forumula: $C_{29}H_{30}O_{13}$
Molecular Mass: 586.55 g/mol
CAS Number: 21018-84-8
ChemSpider ID: 103033
Amarogenin is one of the most bitter compounds known, it is found in gentian root (*Gentiana lutea*).
Parthenolide
IUPAC name: (3aS,9aR,10aS,10bS,E)-6,9a-dimethyl-3-methylene-3a,4,5,8,9,9a,10a,10b-octahydrooxireno[2',3':9,10]cyclodeca[1,2-b]furan-2(3H)-one
Chemical Formula: $C_{15}H_{20}O_3$
Molecular Mass: 248.32 g/mol
CAS Number: 20554-84-1
ChemSpider ID: 20126246
Parthenolide is a sesquiterpene lactone of the germacranolide class which occurs naturally in the plant feverfew (*Tanacetum parthenium*), after which it is named.
Diphenidol
IUPAC name: 1,1-Diphenyl-4-(1-piperidinyl)-1-butanol
Chemical Formula: $C_{21}H_{27}NO$
Molecular Mass: 309.453 g/mol
CAS Number: 972-02-1
ChemSpider ID: 2947
Diphenidol is a muscarinic antagonist employed as an antiemetic and as an anti-vertigo agent. It is not marketed in the United States or Canada. The mechanism of action of diphenidol on the vestibular system has not yet been elucidated.

Apomorphine
IUPAC Name: (6aR)-5,6,6a,7-Tetrahydro-6-methyl-4H-dibenzo(de,g)chinolin-10,11-diol hydrochlorid
Chemical Formula: $C_{17}H_{17}NO_2 \cdot HCl \cdot \frac{1}{2}H_2O$
Molecular Mass: 312.108 g/mol
CAS Number: 41372-20-7
ChemSpider ID: 97017
Apomorphine (brand names Apokyn, Ixense, Spontane, Uprima) is a morphine decomposition product that does not contain morphine or its skeleton, and does not bind to opioid receptors. It does have activity as a non-selective dopamine agonist which activates both D2-like and, to an order of magnitude lesser extent, D1-like receptors. It also acts as an antagonist of 5-HT2 and α-adrenergic receptors with high affinity. It is clinically used for Parkinson's disease, Alzheimer's disease, erectile dysfunction, as well as for alcohol and morphine addiction.

D-Camphor
IUPAC Name: (1R,4R)-4,7,7-trimethylbicyclo[2.2.1]heptan-3-one
Chemical Formula: $C_{10}H_{16}O$
Molecular Mass: 152.237 g/mole
CAS Number: 464-49-3
ChemSpider ID: 139902
Camphor is a waxy, flammable, white or transparent solid with a strong aroma, which is found in the wood of the camphor laurel (Cinnamomum camphora).

Arborescin
IUPAC Name: (4aS,7S,9aS,9bR)-1,4a,7-Trimethyl-5,6,6a,7,9a,9b-hexahydro-3H-oxireno[8,8a]azuleno[4,5-b]furan-8(4aH)-one
Chemical Formula: $C_{15}H_{20}O_3$
Molecular Mass: 248.322 g/mol
CAS Number: 6831-14-7
ChemSpider ID: 16735672
Arborescin is a compound isolated from an endemic plant to the Cape Verde islands Artemisia gorgonum (Asteraceae) Weber.

Artemorin
IUPAC Name: (3aS,7R,10E,11aR)-7-hydroxy-10-methyl-3,6-dimethylidene-4,5,7,8,9,11a-hexahydro-3aH-cyclodeca[b]furan-2-one
Chemical Formula: $C_{15}H_{20}O_3$
Molecular Mass: 248.322 g/mol
CAS Number: 64845-92-7
ChemSpider ID: 4444775
Artemorin is a sesquiterpene lactone isolated from Artemisia genipi Weber.

Divinyl Sulfoxide
IUPAC Name: 1-ethenylsulfinylethene
Chemical Formula: $C_4H_6OS$
Molecular Mass: 102.151 g/mol
CAS Number: 1115-15-7
ChemSpider ID: 13581
Divinyl sulfoxide is the di-unsaturated analog of mustard gas (HD) sulfoxide. Toxicity characteristics similar to that of HD sulfoxide.

Picrotoxinin
IUPAC Name: (1aR,2aR,3S,6R,6aS,8aS,8bR,9R)-2a-hydroxy-8b-methyl-9-(prop-1-en-2-yl)hexahydro-3,6-methano-1,5,7-trioxacyclopenta[ij]cyclopropa[a]azulene-4,8(3H)-dione
Chemical Formula: $C_{15}H_{16}O_6$
Molecular Mass: 292.287 g/mol
CAS Number: 17617-45-7
ChemSpider ID: 16498838
Picrotoxinin is derived naturally in the fruit of the Anamirta cocculus. Due to its interactions with the inhibitory neurotransmitter GABA, picrotoxinin acts as a stimulant and convulsant.

Aristolochic Acid
IUPAC Name: 8-Methoxy-6-nitrophenanthro[3,4-d][1,3]dioxole-5-carboxylic acid
Chemical Formula: $C_{17}H_{11}NO_7$
Molecular Mass: 341.275 g/mol
CAS Number: 313-67-7
ChemSpider ID: 2149
Aristolochic acid is an alkaloid that was originally derived from Aristolochia radix. This compound is a potent phospholipase A2 (PLA2) enzyme inhibitor and also suppresses edema-inducing activity as well as direct and indirect hemolytic activity.

Falcarindiol
IUPAC Name: (3R,8S,9Z)-heptadeca-1,9-dien-4,6-diyne-3,8-diol
Chemical Formula: $C_{17}H_{24}O_2$
Molecular Mass: 260.377 g/mol
CAS Number: 55297-87-5
ChemSpider ID: 4444558
Falcarindiol is a polyacetylene found in carrot roots which has antifungal activity. Falcarindiol is the main compound responsible for bitterness in carrots.

3-caffeoylquinic-1,5-lactone (3-CQL)
IUPAC Name: (1R,3R,4R,5R)-1,4-Dihydroxy-7-oxo-6-oxabicyclo[3.2.1]oct-3-yl (2E)-3-(3,4-dihydroxyphenyl)acrylate
Chemical Formula: $C_{16}H_{16}O_8$
Molecular Mass: 336.293 g/mol
CAS Number: N/A
ChemSpider ID: 30776761
3-caffeoylquinic-1,5-lactone (3-CQL) is a chlorogenic acid lactone, which was found to be the most abundant lactone in in roasted coffee beans of Coffea arabica and Coffea canephora.

Chlorogenic Acid (CGA)
IUPAC Name: (1S,3R,4R,5R)-3-[(E)-3-(3,4-dihydroxyphenyl)prop-2-enoyl]oxy-1,4,5-trihydroxycyclohexane-1-carboxylic acid
Chemical Formula: $C_{16}H_{18}O_9$
Molecular Mass: 354.311 g/mol
CAS Number: 327-97-9
ChemSpider ID: 1405788
Chlorogenic acid (CGA) is the ester of caffeic acid and (−)-quinic acid, functioning as an intermediate in lignin biosynthesis.

A treatment that could utilize a compound with low inherent toxicity to trigger extra-oral bitter receptors in the gut, brain, and other regions such as adipocytes provides a relatively safe means to decrease appetite and increase satiety selectively without the "off-target" CNS effects or GI disturbance typical of other obesity medications.

An ideal bitter compound therapeutic should be safe to consume in the quantities required to elicit the desired physiologic response, and also activate a broad range of TAS2R receptor subtypes. Denatonium benzoate (DB) and 3-CQL are bitter substances that activate eight TAS2R subtypes. It is also generally regarded as safe and is commercially added to toxic household products to discourage inadvertent consumption by children. Quinine is also an ingested alkaloid that is safe in small quantities and found in soda water and used as an anti-malarial medication. It activates nine TAS2R subtypes.

Coating a bitter compound, such as DB or quinine, in a tasteless ingestible capsule allows a pharmaceutical composition to bypass induction of aversive responses mediated by oral TAS2R receptors. But it still provides anorexigenic effects via stimulation of gut receptors, brain and adipocyte TAS2R receptors, after absorption into the circulation.

In another embodiment, the bitter agent is apomorphine, which is a breakdown product of morphine. It is used currently as a drug for Parkinson's disease, but delivered subcutaneously. Apomorphine oral availability is approximately only 4%. It has a current veterinary use as an agent to induce vomiting in dogs. Aside from also being a bitter alkaloid, it also is a dopamine agonist (D2 receptor). Therefore, the present disclosure provides an oral formulation of apomorphine, even with its intrinsically low oral availability, since targeting of gut TAS2R receptors would represent the primary intended mechanism of action.

As is the case with receptors to detect bitterness, receptors detecting sweet compounds are not only located in the oral cavity. Without being bound by theory, the T1R2/T1R3 sweet receptor is found on K- and L-type enteroendocrine cells in the intestine. When such receptors are activated, the enteroendocrine cells secrete incretins such as glucagon-like peptide-1 (GLP-1) which in turn stimulate insulin secretion. This effect is seen even with artificial sweeteners, which can lead to undesirable metabolic effects. This T1R2/T1R3 mediated phenomenon is sufficiently profound that orally ingesting glucose typically triggers a greater release of insulin than injecting the same amount of glucose directly into the bloodstream. Moreover, cells adjacent to L-cells that detect sweetness increase expression of a glucose transporter to accelerate absorption of sugar from the gut to the blood; rapidity of sugar absorption is associated with insulin resistance and diabetes. Stomach T1R receptors also trigger the release of ghrelin, which serves to increase hunger.

Thus, there is a surprising discovery that compounds that can block T1R2/T1R3 sweet receptors can synergistically suppress appetite and delay gastric emptying (increasing and prolonging satiety) when used in conjunction of TAS2R agonist bitter agents. There are several compounds to effectively block T1R receptor activation:

Lactisole—a Generally Recognized as Safe (GRAS) compound (Flavor and Extract Manufacturers Association (FEMA) number is "3773") commercially used as an additive to blunt foods such as fruit jams that would otherwise be perceived as overly sweet. Lactisole is used in concentrations of 50 ppm to 150 ppm for and is also naturally found in Colombian Arabica coffee beans.

Gymnemic Acid—found in an Indian vine.

Ziziphin—from the jujube plant.

Hodulcine—from the Japanese raisin plant.

A clinical use for a combination orally ingested tablet or pill containing a bitter agent in combination with a sweet receptor antagonist beyond obesity is Prader-Willi Syndrome. Among the key hallmarks of this genetic disorder is a constant hunger drive and a lack of sense of satiety even after eating copious amounts of food. Therefore, the present disclosure provides a method for treating Prader-Willi Syndrome (PWS) comprising an anti-obesity oral formulation comprising (a) a bitter agent selected from the group consisting of denatonium benzoate (DB), denatonium chloride, denatonium saccharide, quinine, chloroquine, cromolyn, diphenidol, amarogentin, apomorphine, parthenolide, camphor, arborescin, artemorin, divinyl sulfoxide, picrotoxinin, aristolochic acid, falcarindiol, 3-caffeoylquinic-1,5-lactone (3-CQL), chlorogenic acid (CGA), and combinations thereof; (b) a sweet antagonist selected from the group consisting of lactisole, gymnemic acid, ziziphin, hodulcine, and combinations thereof; and (c) pharmaceutical excipients to facilitate a sustained release during transit through the GI tract. Preferably, the oral formulation further comprises an organic acid selected from the group consisting of acetic acid, malic acid, maleic acid, citric acid and combinations thereof.

Example 1

This example describes a method for formulating a Denatonium Benzoate/Lactisole/Acetic Acid Extended Release Tablet, 44.6 mg/20 mg/500 mg.

| Ingredient | Per dose[1], mg | Quantity, kg |
|---|---|---|
| Denatonium Benzoate | 44.6 | 5.575 |
| Lactisole | 20 | 2.5 |
| Acetic Acid, NF (36.5% w/w) | 1370 | 171.25 |
| Microcrystalline Cellulose | 100 | 12.5 |
| Mannitol | 80 | 10 |
| Polyvinyl Pyrrolidone 30 (PVP 30) | 38 | 4.75 |
| Magnesium Stearate | 4 | 0.5 |
| Ethylcellulose aqueous dispersion (Aquacoat ECD 30, FMC). | 786.7 | 98.34 |
| Dibutyl Sebacate | 59 | 7.375 |

[1]A dose can be from one to five tablets.

Add microcrystalline cellulose (Avicel PH101), denatonium benzoate, lactisole, PVP 30 (half quantity) and mannitol to a 10 cubic feet V-blender and mix for 10 minutes. Transfer the blend to a high shear granulator and start granulating with a controlled spray rate of acetic acid (half quantity) at 800 g/minute. After granulation, the wet granules are removed and placed in a tray dryer controlled at 50° C. for a period until the final moisture content is below 2% w/w. The dried granules are subsequently passed through a Fitzmill equipped with 18 mesh screen. The milled granules are then placed back to the same high shear granulator and add the remaining half of the PVP 30 and again granulating with the remaining half of the acetic acid. The wet granules are removed and dried at 50° C. until the moisture content is below 2%. The dried granules are milled in a Fitzmill with 18 mesh screen, and then mixed with Magnesium Stearate in a 10 cubic feet V-blender for 5 minutes and the final blends are compressed in a tablet press with target 786.6 mg weight and 10 kp hardness (Uncoated Tablets).

The coating solution is prepared by dispersing dibutyl sebacate in the Aquacoat ECD 30 dispersion and gently mix for 1 hour. The Uncoated Tablets are loaded in a pan coater and sprayed with the Coating Solution at a controlled spray rate of 80 g/min. Continue drying for 30 minutes after the coating is complete.

Example 2

This example describes a method of Denatonium Benzoate/Lactisole/Acetic Acid Immediate Release Tablet, 22.3 mg/10 mg/250 mg.

| Ingredient | Per dose[2], mg | Quantity, kg |
|---|---|---|
| Denatonium Benzoate | 22.3 | 4.46 |
| Lactisole | 10 | 2 |

-continued

| Ingredient | Per dose[2], mg | Quantity, kg |
|---|---|---|
| Acetic Acid, NF (36.5% w/w) | 685 | 137 |
| Microcrystalline Cellulose | 100 | 20 |
| Mannitol | 90.2 | 18.04 |
| Polyvinyl Pyrollidone 30 (PVP 30) | 25 | 5 |
| Magnesium Stearate | 2.5 | 0.5 |

[2]A dose can be from one to five tablets.

Add microcrystalline cellulose (Avicel PH101), denatonium benzoate, lactisole, PVP 30 (half quantity) and mannitol to a 10 cubic feet V-blender and mix for 10 minutes. Transfer the blend to a high shear granulator and start granulating with a controlled spray rate of acetic acid (half quantity) at 800 g/minute. After granulation, the wet granules are removed and placed in a tray dryer controlled at 50° C. for a period until the final moisture content is below 2% w/w. The dried granules are subsequently passed through a Fitzmill equipped with 18 mesh screen. The milled granules are then placed back to the same high shear granulator and add the remaining half of the PVP 30 and again granulating with the remaining half of the acetic acid. The wet granules are removed and dried at 50° C. until the moisture content is below 2%. The dried granules are milled in a Fitzmill with 18 mesh screen and then mixed with Magnesium Stearate in a 10 cubic feet V-blender for 5 minutes and the final blends are compressed in a tablet press with target 500 mg weight and 10 kp hardness.

Example 3

This example provides the results of an unblinded open clinical study with one participant who self-administered a disclosed formulation of denatonium benzoate (DB) at a dose of 20 mg orally (PO) once daily (QD) and lactisol at a dose of 50 mg PO QD weighed into a gel capsule without excipients. Each capsule contained 20 mg of DB (dose of DB started at 1 mg and escalated to 20 mg over the initial week) and 50 mg of lactisol. One capsule was taken orally with water in the morning around 5:30 am. The result is that the participant (who was not initially overweight) was able to lose around 20 lbs over the course of 30 days. In view of a need to cease losing weight, the disclosed formulation was discontinued and the participant's weight stabilized.

Example 4

This example provides the results of an oral dose rat gavage study, measuring food and water intake following administration of a disclosed formulation by gavage. We conducted an acute food intake inhibition study of DB in Sprague Dawley rats. Various doses of DB significantly inhibited food intake within the first 6 h after administration, but this was not the case at 8 h and 24 h after administration. These results indicate that DB may have a half-life of only 6 h.

For a longer term study, in view of the foregoing acute study findings, the effect of a combination of components was investigated. To ensure the adequate effect of the DB combination, 60 μmol/kg (26.8 mg/kg) once daily for DB in the first two weeks of the study was used, and then switched to twice daily in the last two weeks of the study. FIG. 1 shows average cumulative food consumption over 24 hours measured for the acute study measured a times 0, 2, 4, 6, 8 and 24 hours after a single administration of the disclosed formulation. FIG. 1 shows that at all time points in the first 8 hours, the rats given water control consumed significantly more food that the disclosed formulation rats.

Example 5

This example provides the results of an oral dose administration in DIO C57BL/6NTac mice study of the effects of denatonium benzoate and its combination with sweet taste blocker and sour taste stimulator, measuring food intake, body weight and obesity-related metabolic disorders. C57BL/6NTac male mice (16-week age, weighing 37-49 g) on 60% kcal high fat irradiated diet (D12492) are provided by Taconic Biosciences. Denatonium benzoate (5 g, purity≥99%) was obtained from Santa Cruz Biotechnology (Cat No. sc-234525). Lactisole (10 g, purity≥98%) was obtained from Cayman Chemical, Inc. (Cat No. 18657). Acetic acid (food grade, purity≥99.5%) was obtained from Sigma-Aldrich (Cat No. W200611). A 1% solution (w/v) was used for the study. The mice were housed in individual clear plastic cages with sawdust bedding. High-fat, purified 12492 diet (60% kcal fat, 12.5 kg, Cat No. #D12492) is provided by Research Diets Inc.

Two experimental groups were studied. One control group received only distilled water. One treatment group received the disclosed the formulation comprising DB 60 μmol/kg (26.8 mg/kg), lactisol (0.1 mmol/kg) and 5 ml/kg acetic acid (1% w/v). The formulation or water was administered by gavage twice daily.

Upon arrival at the facility, the mice were singly housed with label cage cards with both study and animal numbers. Animals will be allowed ad libitum access to diet and water. Maintain the housing room at a constant humidity (60% to 70%) and temperature (22 to 24° C.) with a fixed light/dark schedule (e.g. dark cycle for 7 h from 10:00 AM). Bedding changed every 3 to 4 days. After 3-day habituation to the shift of light/dark schedule, animals that weighed between 30 and 45 g were chosen for the study. At the start of the study, 22 male C57BL/6NTac mice were randomly allocated to one of two weight-matched treatment groups, each containing 11 animals: Control (treated with vehicle (distilled water)), and DB-Combination (treated with 26.8 mg/kg DB, 0.1 mmol/kg lactisole, and 5 ml/kg 1% acetic acid). Then, all animals underwent a 5-day period of habituation to oral gavage dosing (twice daily, one will be at the beginning of lights off, the other at the end of lights off). During the habituation period, all animals had ad libitum access to water and diet.

At the day of treatment initiation (Day 0), all animals were weighed 2 h prior to lights off and allowed free access to water but no food during this period. Afterwards, vehicle (distilled water) and the DB combination (26.8 mg/kg DB, 0.1 mmol/kg lactisole, and 5 mL/kg 1% acetic acid) were administered just before lights off. Then, all mice were allowed access to a pre-weighed amount of high fat diet (approximately double mean daily intake, 10 to 15 g) and water. At the end of lights off, all animals received a second administration. From the next day, body weight and 24 h food intake was measured at the same time each day, preferably within 2 h prior to dark phase initiation. 24 h food intake was calculated by subtracting each daily food weight from the previous day's weight. Dosing was continued for 28 days (4 weeks)

At the beginning (Day 0-2) and the end of the study (Day 28-30), blood was sampled from the lateral tail vein of all animals after fasting overnight. For each animal, about 100 μL of blood was collected. Afterwards, serum was isolated from the collected blood samples, and the serum levels of glucose, HbA1c, insulin, and LDL cholesterol examined using the corresponding kits according to the protocols provided by the manufacturer.

Figure 2:
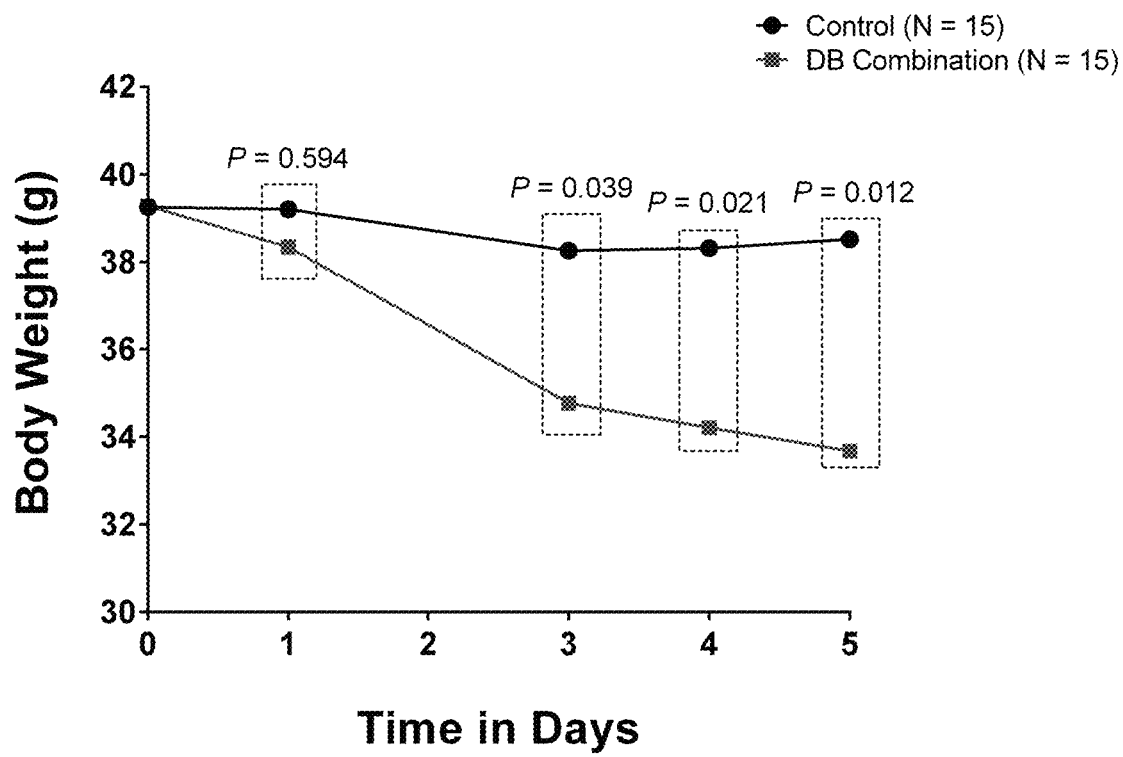
FIG. 2 shows average body weight measurements over 5 days after daily administration of the disclosed formulation in diet-induced obese (DIO) C57BL/6NTac male mice. The figure shows that the disclosed formulation caused a significant weight loss versus water control.

FIG. 2 shows average body weight measurements over 5 days after daily administration of the disclosed formulation in DIO C57BL/6NTac male mice. FIG. 2 shows that the disclosed formulation caused a significant weight loss versus water control.

Figure 3:
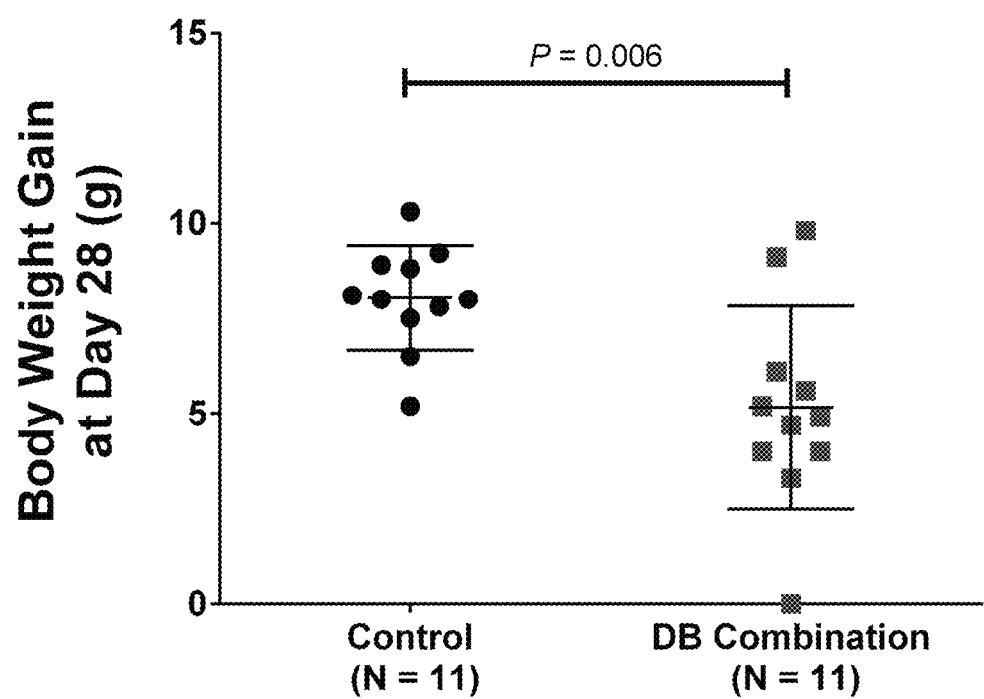
FIG. 3 shows the average weight gains of DIO C57BL/6NTac male mice on a 60% kcal high fat irradiated diet (D12492) during a 28-day dosing study comparing the disclosed formulation administered orally versus distilled water. While both groups of mice gained weight during the course of the study, the water control mice gained much more weight.

FIG. 3 shows the average weight gains of the DIO C57BL/6NTac mice on a 60% kcal high fat irradiated diet (D12492) during the 28 day dosing study comparing the disclosed formulation administered orally versus distilled water. While both groups of mice gained weight during the course of the study, the water control mice gained much more weight.

Figure 4:
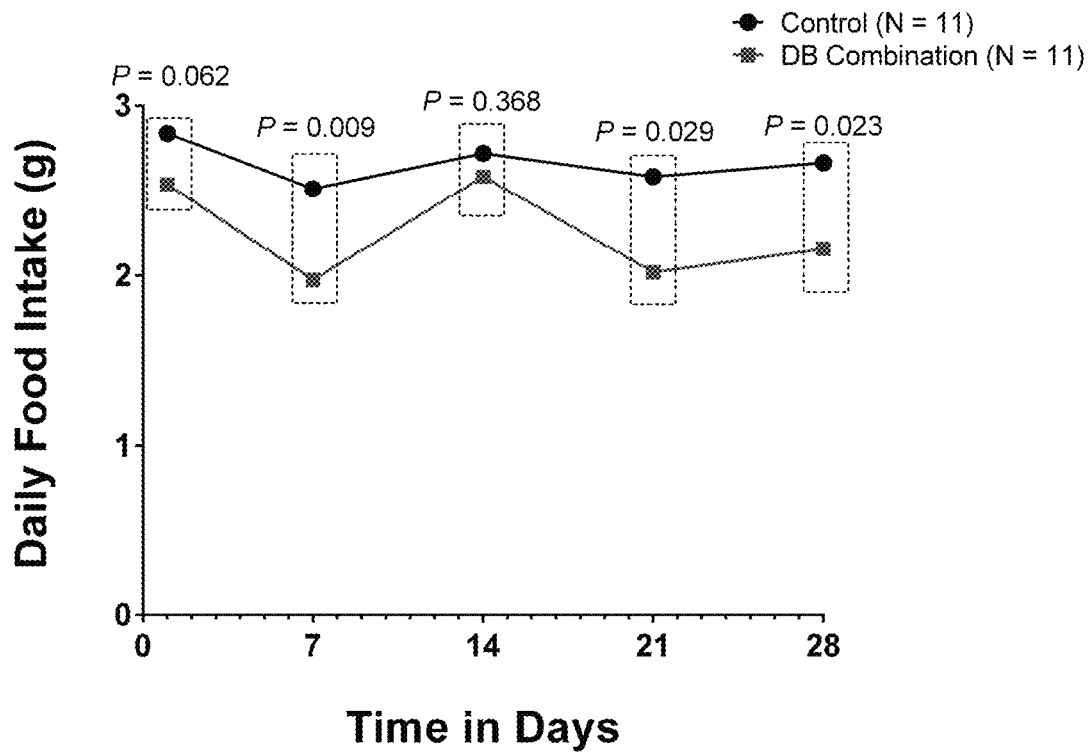
FIG. 4 shows average cumulative food consumption for DIO C57BL/6NTac male mice over the course of the 28-day study. The water control mice consumed more food.

FIG. 4 shows average cumulative food consumption for the DIO C57BL/6NTac mice over the course of the 28 day study. The water control mice consumed more food.

Figure 5:
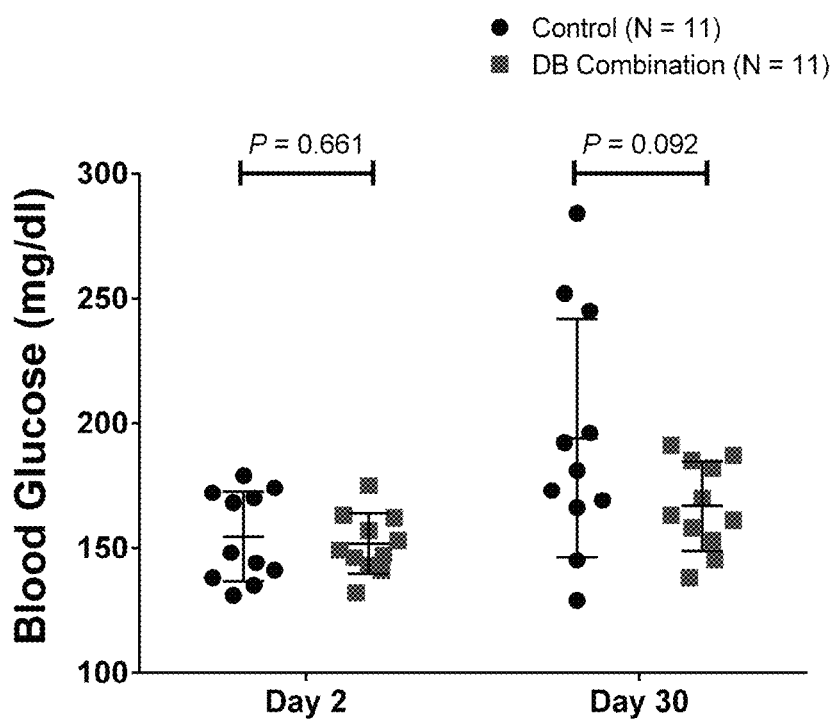
FIG. 5 shows a bar graph of average blood glucose taken at day 2 and day 30 of the study with DIO C57BL/6NTac mice. While blood glucose levels were similar for both groups at day 2, by day 30 blood glucose had risen more slowly in the disclosed formulation group than in the water control group.

FIG. 5 shows a bar graph of average blood glucose taken at day 2 and day 30 of the study with the DIO C57BL/6NTac mice. While blood glucose levels were similar for both groups at day 2, by day 30 blood glucose had risen more slowly in the disclosed formulation group than in the water control group.

Figure 6:
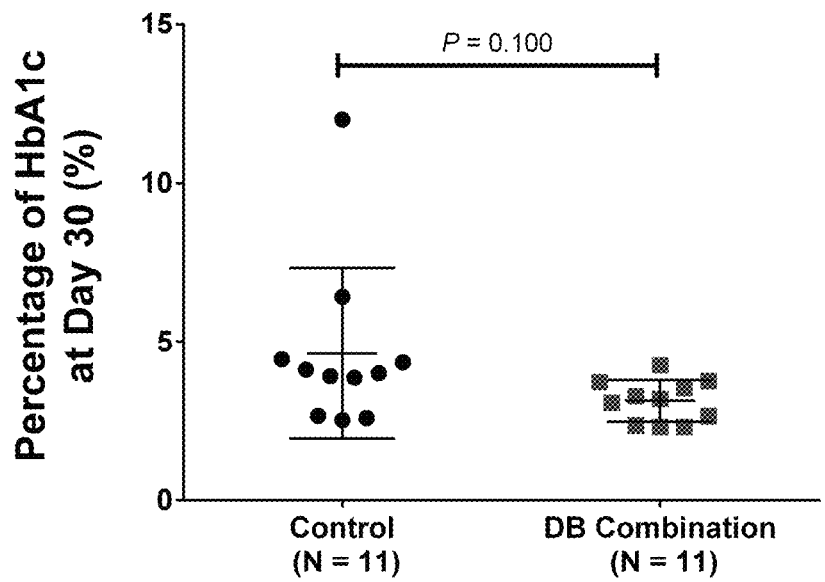
FIG. 6 shows that hemoglobinA1c levels on day 30 had fallen for the disclosed formulation mice versus the control water mice. This is a key measure of glycemic control in diabetes.

FIG. 6 shows that HbA1c levels on day 30 had fallen for the disclosed formulation mice versus the control water mice. This is a key measure of glycemic control in diabetes.

Figure 7:
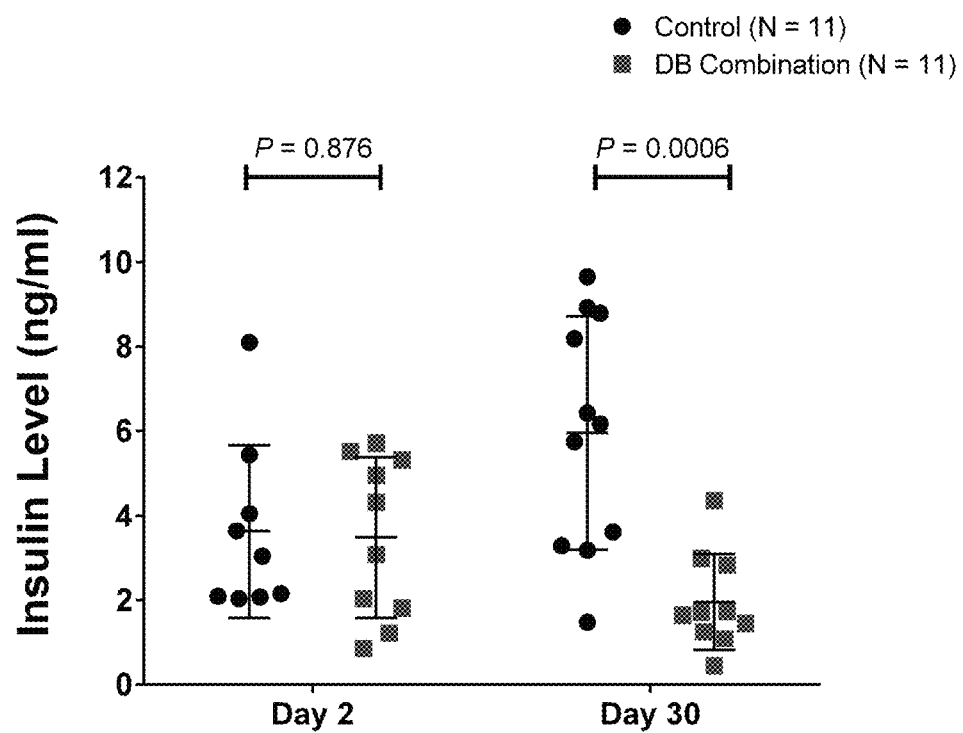
FIG. 7 is a bar chart comparing blood insulin levels at days 2 and 30 in the DIO C57BL/6NTac mice. While insulin levels were somewhat lower at day 2, the disclosed formulation mice shows much lower insulin levels at day 30 as compared to the water control mice, indicating an overall improvement in metabolism.

FIG. 7 is a bar chart comparing blood insulin levels at days 2 and 30 in the DIO C57BL/6NTac mice. While insulin levels were somewhat lower at day 2, the disclosed formulation mice show much lower insulin levels at day 30 as compared to the water control mice, indicating an overall improvement in metabolism. Without being bound by theory with regard to a postulated mechanism of action, while the weight loss or reduced weight gain of the treated mice is presumed to be due to reduced calorie consumption, the demonstrated effect or reduced insulin levels (see FIG. 7) or other metabolic changes could be the mechanism of action for the weight loss experienced by the disclosed formulation.

Figure 8:
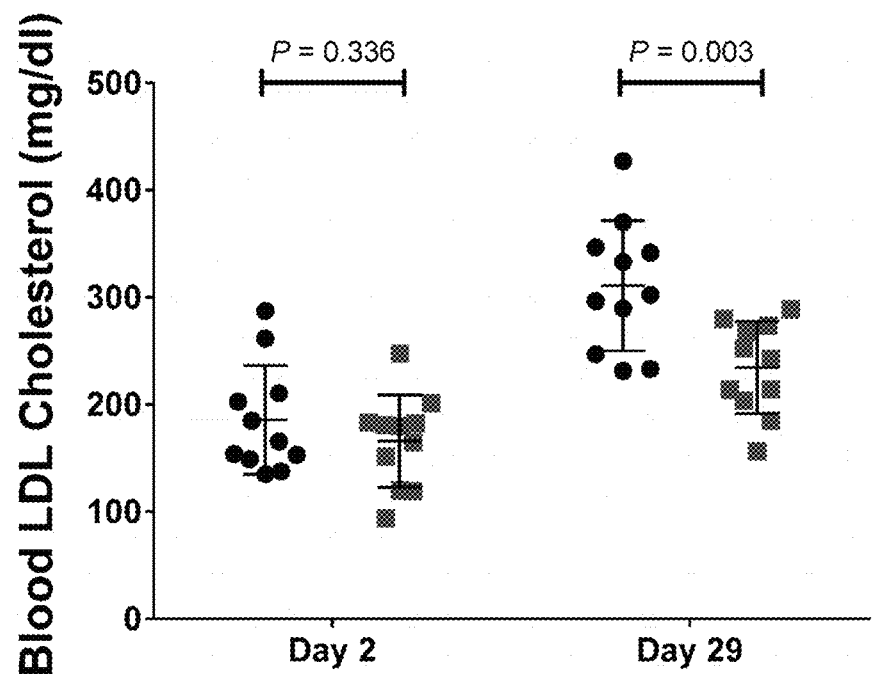
FIG. 8 shows a bar graph of average blood LDL cholesterol level taken at day 2 and day 29 of the study with DIO C57BL/6NTac mice. While blood LDL cholesterol levels were similar for both groups at day 2, by day 29 blood LDL cholesterol had risen more slowly in the disclosed formulation group than in the water control group.

FIG. 8 shows a bar graph of average blood LDL cholesterol level taken at day 2 and day 29 of the study with DIO C57BL/6NTac mice. While blood LDL cholesterol levels were similar for both groups at day 2, by day 29 blood LDL cholesterol had risen more slowly in the disclosed formulation group than in the water control group.

Example 6

This example illustrates a synthesis of various bitter agents provided herein.

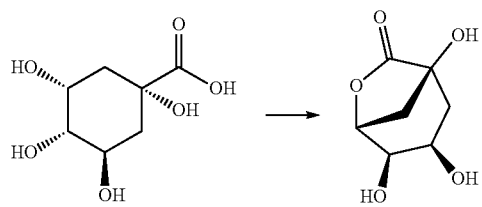 [SMILES: O=C(O)[C@]1(O)C[C@@H](O)[C@@H](O)[C@H](O)C1 ; O=C1O[C@@H]2C[C@@]1(O)C[C@@H](O)[C@H]2O]

1,5-quinide. Quinic acid (25 g, 130.1 mmol) and p-toluenesulfonic acid (500 mg, 2.622 mmol) were dissolved in anhydrous toluene (350 mL) and dimethylformamide (50 mL) in an oven-dried round bottom flask. The flask was equipped with a Dean-Stark apparatus and the vessel was refluxed overnight while stirring. The mixture was cooled to room temperature and toluene was evaporated. The remaining solution was cooled in an ice bath and solid was precipitated by the addition of a hexanes and ethyl acetate mixture (4:1). The precipitate was filtered and rinsed with diethyl ether to give a white solid (6.078 g, 26.8% yield). $^1$H NMR (600 MHz, Methanol-$d_4$) δ 4.70 (dd, J=6.0, 4.9 Hz, 1H), 3.98 (t, J=4.6 Hz, 1H), 3.70 (ddd, J=11.2, 6.6, 4.4 Hz, 1H), 2.47 (d, J=11.4 Hz, 1H), 2.22 (ddd, J=11.4, 6.0, 3.0 Hz, 1H), 2.03 (dddd, J=11.8, 6.6, 2.9, 0.8 Hz, 1H), 1.87 (t, J=11.6 Hz, 1H).

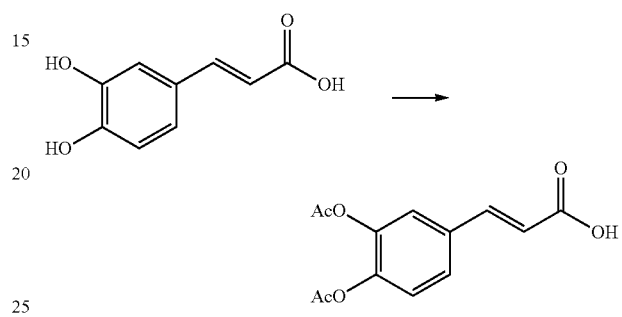

3,4-Diacetoxycinnamic acid. A mixture of caffeic acid (25 g, 138.8 mmol) and pyridine (11.18 mL, 138.8 mmol) was added acetic anhydride (65.59 mL, 603.8 mmol) and stirred at room temperature overnight. The solvent was evaporated and the solid was rinse with water followed by diethyl ether and dried to obtain a white solid (19.56 g, 53.3%). $^1$H NMR (600 MHz, DMSO-$d_6$) δ 12.48 (broad s, 1H), 7.66 (d, J=2.1 Hz, 1H), 7.63 (dd, J=8.4, 2.1 Hz, 1H), 7.56 (d, J=16.0 Hz, 1H), 7.31 (d, J=8.3 Hz, 1H), 6.53 (d, J=16.0 Hz, 1H), 2.29 (d, J=4.4 Hz, 6H).

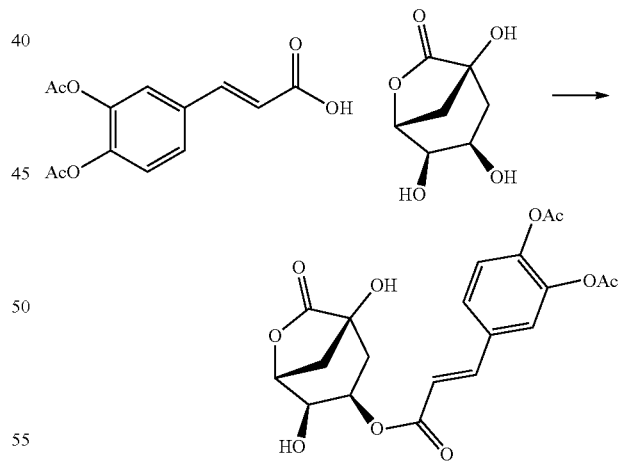

3,4-Diacetoxycinnamoylquinic acid lactone. To 3,4-diacetoxycinnamic acid (4 g, 15.14 mmol) suspended in anhydrous dichloromethane (70 mL) under argon was added oxalyl chloride (1.3 mL, 15.14 mmol) followed by anhydrous DMF (0.6 mL). The reaction stirred for two hours and the solution became transparent. 1,5-quinide and 4-Dimethylaminopyridine dissolved in a pyridine dichloromethane mixture (1:2.5, 140 mL) was added to the reaction vessel. The mixture was warmed to 35° C. and stirred for 4 hours. The solvent was evaporated and the solid was purified by flash chromatography (DCM/MeOH 4%) to yield a white solid (3.605 g, 56.7%). $^1$H NMR (600 MHz, Chloroform-d) δ 7.66 (d, J=15.9 Hz, 1H), 7.40 (ddd, J=8.4, 2.1, 0.5 Hz, 1H), 7.37 (d, J=2.1 Hz, 1H), 7.23 (d, J=8.3 Hz, 1H), 6.39 (d, J=16.0 Hz, 1H), 5.06 (ddd, J=11.3, 6.9, 4.3 Hz, 1H), 4.84 (dd, J=6.0, 4.9 Hz, 1H), 4.38 (board s, J=2.7 Hz, 1H), 2.71 (d, J=11.8 Hz, 1H), 2.57 (d, J=2.9 Hz, 1H), 2.36 (ddd, J=11.8, 6.0, 2.8 Hz, 1H), 2.30 (d, J=2.3 Hz, 6H), 2.26 (ddd, J=12.7, 6.9, 2.9, 0.8 Hz, 1H).

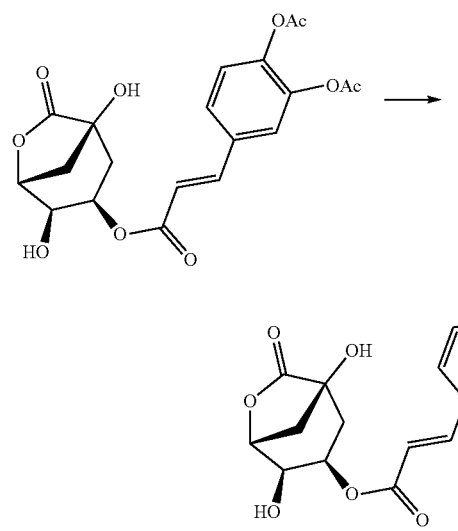

3-Caffeoyl-1,5-quinide. To a solution of 3,4-Diacetoxycinnamoylquinic acid lactone (3 g, 7.137 mmol) in Ethanol (60 mL) was added ammonium hydroxide (1.5 mL, 14.8 M) and was stirred for 1 hour. Acidified with hydrochloric acid (1M) and extracted with ethyl acetate. The organic extractions were dried over sodium sulfate, filtered and the solvent was evaporated. The solid was recrystallized from hot ethyl acetate to obtain a white solid (1.725 g, 71.9%). $^1$H NMR (600 MHz, Methanol-d$_4$) δ 7.62 (d, J=15.9 Hz, 1H), 7.05 (d, J=2.1 Hz, 1H), 6.96 (dd, J=8.3, 2.1 Hz, 1H), 6.78 (d, J=8.2 Hz, 1H), 6.30 (d, J=15.9 Hz, 1H), 4.91 (ddd, J=11.4, 6.8, 4.3 Hz, 1H), 4.74 (dd, J=6.0, 5.0 Hz, 1H), 4.29 (t, J=4.6 Hz, 1H), 2.56 (d, J=11.6 Hz, 1H), 2.30 (ddd, J=11.5, 6.0, 2.8 Hz, 1H), 2.19-2.13 (m, 1H), 2.08 (t, J=11.7 Hz, 1H).

Example 7

Synthesis of Denatonium Acetate

Step 1: Synthesis of Denatonium Hydroxide from Lidocaine

To a reflux apparatus add 25 g of lidocaine, 60 ml of water and 17.5 g of benzyl chloride with stirring and heating in 70-90° C. The solution needs to be heated and stirred in the before given value for 24 h, the solution needs to be cooled down to 30° C. The unreacted reagents are removed with 3×10 mL of toluene. With stirring dissolve 65 g of sodium hydroxide into 65 mL of cold water and add it to the aqueous solution with stirring over the course of 3 h. Filter the mixture, wash with some water and dry in open air. Recrystallize in hot chloroform or hot ethanol.

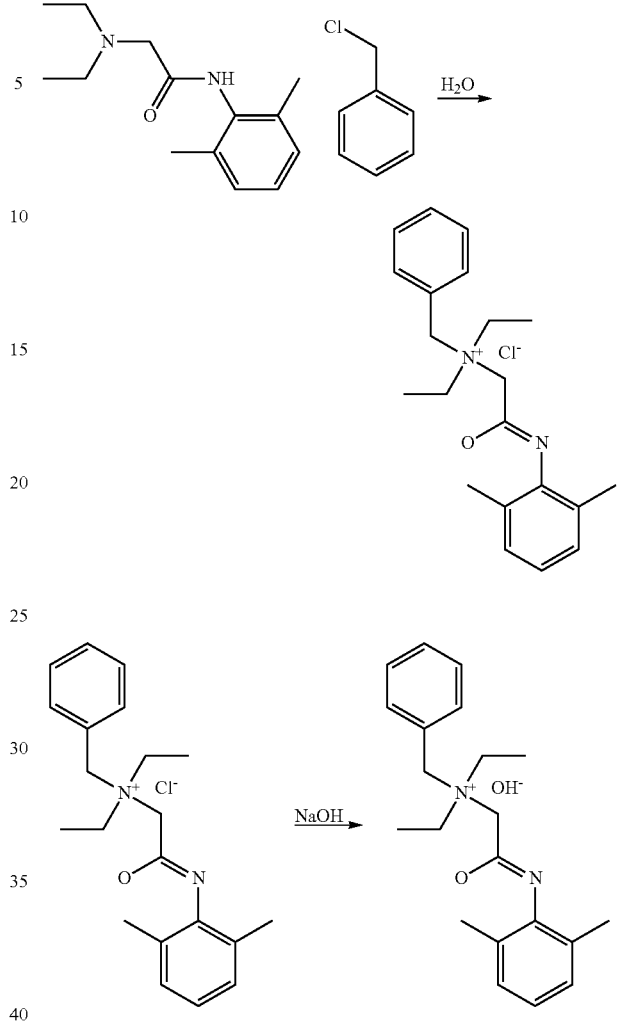

Step 2: Preparation of Denatonium Acetate from Denatonium Hydroxide.

To a reflux apparatus 10 g of denatonium hydroxide (MW: 342.475 g/mol, 0.029 mol), 20 mL of acetone, and 2 g of acetic acid glacial (0.033 mol) dissolved in 15 mL of acetone is added, the mixture is stirred and heated to 35° C. for 3 h. Then evaporated to dryness and recrystallized in hot acetone.

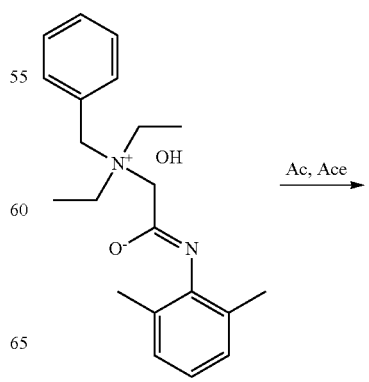

-continued

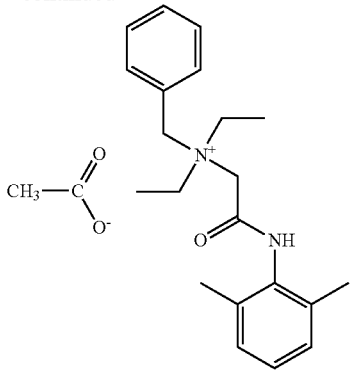

I claim:

1. An oral formulation comprising a bitter agent selected from the group consisting of denatonium acetate (DA), denatonium citrate (DC), denatonium tartarate (DT), denatonium maleate (DM), and combinations thereof; and a coating excipient or capsule, whereby the oral formulation dissolves in the stomach or lower.

2. The formulation of claim 1 further comprising either or both a sweet antagonist selected from the group consisting of lactisole, gymnemic acid, ziziphin, hodulcine, and combinations thereof, and a sour organic acid.

3. The formulation of claim 1 further comprising pharmaceutical excipients to facilitate a sustained release during transit through the GI tract.

4. The formulation of claim 2, wherein the organic acid selected from the group consisting of acetic acid, malic acid, maleic acid, citric acid and combinations thereof.

5. The formulation of claim 1, wherein the daily dosage of DA or DC for an adult is from about 10 mg to about 400 mg.

6. The formulation of claim 5, wherein the daily dosage of DA or DC for an adult is from about 10 mg to about 200 mg.

7. The formulation of claim 6, wherein the daily dosage of DA or DC for an adult is from about 10 mg to about 100 mg, or to achieve a concentration in the GI tract of from about 10 parts per billion to about 10 ppm.

8. A method for effecting weight loss, comprising administering an anti-obesity oral formulation comprising a bitter agent selected from the group consisting of denatonium acetate (DA), denatonium citrate (DC), denatonium tartarate (DT), denatonium maleate (DM), and combinations thereof; and a coating excipient or capsule, whereby the oral formulation dissolves in the stomach or lower.

9. The method for effecting weight loss of claim 8 further comprising further administering either a sweet antagonist selected from the group consisting of lactisole, gymnemic acid, ziziphin, hodulcine, and combinations thereof; or an organic acid selected from the group consisting of acetic acid, malic acid, maleic acid, citric acid and combinations thereof; and pharmaceutical excipients to facilitate a sustained release during transit through the GI tract.

10. The method for effecting weight loss of claim 8, wherein the bitter agent is DA or DC.

11. The method for effecting weight loss of claim 10, wherein the daily dosage of DA or DC for an adult is from about 10 mg to about 400 mg.

12. The method for effecting weight loss of claim 11, wherein the daily dosage of DA or DC for an adult is from about 10 mg to about 200 mg.

13. The method for effecting weight loss of claim 12, wherein the daily dosage of DA or DC for an adult is from about 10 mg to about 100 mg, or to achieve a concentration in the GI tract of from about 10 parts per billion to about 10 ppm.

14. A method for treating adult onset diabetes as measured by HbA1c and or insulin and or low density lipoprotein (LDL) cholesterol levels, comprising administering a bitter agent selected from the group consisting of denatonium acetate (DA), denatonium citrate (DC), denatonium tartarate (DT), denatonium maleate (DM), and combinations thereof; and a coating excipient or capsule, whereby the oral formulation dissolves in the stomach or lower.

15. The method for treating adult onset diabetes of claim 14, further comprising further administering either a sweet antagonist selected from the group consisting of lactisole, gymnemic acid, ziziphin, hodulcine, and combinations thereof; or an organic acid selected from the group consisting of acetic acid, malic acid, maleic acid, citric acid and combinations thereof; and pharmaceutical excipients to facilitate a sustained release during transit through the GI tract.

16. The method for treating adult onset diabetes of claim 14, wherein the bitter agent is DA or DC.

17. The method for treating adult onset diabetes of claim 16, wherein the daily dosage of DA or DC for an adult is from about 10 mg to about 400 mg.

18. The method for treating adult onset diabetes of claim 17, wherein the daily dosage of DA or DC for an adult is from about 10 mg to about 200 mg.

19. The method for treating adult onset diabetes of claim 18, wherein the daily dosage of DA or DC for an adult is from about 10 mg to about 100 mg, or to achieve a concentration in the GI tract of from about 10 parts per billion to about 10 ppm.

* * * * *